(12) United States Patent
Peterson et al.

(10) Patent No.: US 6,596,725 B2
(45) Date of Patent: Jul. 22, 2003

(54) USE OF CERTAIN DINUCLEOTIDES TO STIMULATE REMOVAL OF FLUID IN RETINAL DETACHMENT AND RETINAL EDEMA

(75) Inventors: Ward M. Peterson, Durham, NC (US); Benjamin R. Yerxa, Raleigh, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/774,752

(22) Filed: Jan. 30, 2001

(65) Prior Publication Data

US 2001/0031743 A1 Oct. 18, 2001

Related U.S. Application Data (63) Continuation-in-part of application No. 09/101,395, filed as application No. PCT/US98/02702 on Feb. 6, 1998, which is a continuation-in-part of application No. 08/798,508, filed on Feb. 10, 1997, now Pat. No. 5,837,861.

(51) Int. Cl.[7] .......................... A61K 9/00; C07H 21/04
(52) U.S. Cl. .................. 514/256; 514/299; 514/912; 514/51; 514/42; 514/43; 514/44; 514/49; 514/47; 536/25.6; 536/26.1
(58) Field of Search ................. 514/256, 299, 514/912, 51, 42, 43, 44, 49, 47; 536/25.6, 26.1

(56) References Cited

U.S. PATENT DOCUMENTS 6,040,297 A    3/2000  De Flora et al.
6,277,855 B1 * 8/2001  Yerxa
6,323,187 B1 * 11/2001 Yerxa et al. .................. 514/51
6,348,589 B1 * 2/2002  Pendergast et al. ........ 536/25.6

FOREIGN PATENT DOCUMENTS

WO    WO 98/34593    8/1998
WO    WO 98/34942    8/1998
WO    WO 00/30629    6/2000
WO    WO 01/87913    11/2001

OTHER PUBLICATIONS

Peterson, et al, J. Neurosci. 17(7):2324–37 (1997).
A. Moss and V. Parsons, *National Center for Health Statistics*, 1986:66–7, DHHS Publication No. (PHS) 86–1588 (1985).
J. Klein, *Clin. Infect. Dis.* 19, 823–33 (1994).
M. Lethem, et al., *Am. J. Respir. Cell Mol. Biol.* 9, 315–22 (1993).

(List continued on next page.)

*Primary Examiner*—Samuel Barts
*Assistant Examiner*—Devesh Khare
(74) *Attorney, Agent, or Firm*—Albert P. Halluin; Viola T. Kung; Howrey, Simon, Arnold & White, L.L.P.

(57) ABSTRACT

The present invention provides a method of treating edematous retinal disorders. The method comprises administration of a P2Y receptor agonist to stimulate the removal of pathological extraneous fluid from the subretinal and retinal spaces and thereby reduce the accumulation of said fluid associated with retinal detachment and retinal edema. The P2Y receptor agonist may be administered with therapeutic and adjuvant agents commonly used to treat edematous retinal disorders. The pharmaceutical composition useful in this invention comprises a P2Y receptor agonist with enhanced resistance to extracellular hydrolysis, such as dinucleoside polyphosphate compounds.

34 Claims, 7 Drawing Sheets

OTHER PUBLICATIONS

D. Drutz, et al., *Drug Dev. Res.* 37(3), 185 (1996).
S. Mason, et al., *Br. J. Pharmacol.* 103, 1649–56 (1991).
L. Gobran, *Am. J. Physiol.* 267, L625–L633 (1994).
M. Knowles, et al., *N. Engl. J. Med.* 325, 533–38 (1991).
H. Brown, et al., *Mol. Pharmocol.* 40, 648–55 (1991).
K. Olivier, et al., *Am. J. Respr. Crit. Care Med.* 154, 217–23 (1996).
P. Noone, et al., *Am. J. Respir. Crit. Care Med.* 153, A530 (1996).
E. Lazarowski, E., et al., *Brit. J. Pharm.*, 116, 1619–27 (1995).
C. McKenna, et al., *J. Org. Chem.* 46, 4574–76 (1980).
D. Burton, et al., *J. Fluorine Chem.* 15, 263–266 1980.
M.A.G. Sillero, et al., *Eur. J. Biochem.*, 76, 331 (1977).
C.G. Vallejo, et al., *Biochem. Biophy. Acta*, 483, 304 (1976).
H. Coste, et al., *J. Biol. Chem.*, 262, 12096 (1987).
K.E. Ng, et al., *Nucleic Acid Res.*, 15, 3573 (1987).
J. Stepinski, et al., *Nucleosides & Nucleotides*, 14, 717 (1995).
A. Zatorski, et al., *J. Med. Chem.*, 39, 2422 (1996).
P. Rotilan, et al., *FEBS*, 280, 371 1991.
P.C. Zamecnik, et al., *Proc. Natl. Acad. Sci.*, 89, 2370 1992.
J. Walker, et al., *Biochemistry*, 32, 14009 (1993).
R.H. Hiderman, et al., *J. Biol. Chem.*, 266, 6915 (1991).
J. Luthje, et al., *Eur. J. Biochem.*, 173, 241 (1988).
R.H. Silverman, et al., *Microbiological Rev.*, 43, 27 (1979).
C.D. Lobaton, et al., *Eur. J. Biochem.*, 50, 495 (1975).
G. Lowe, et al., *Nucelosides & Nucleotides*, 10, 181 (1991).
G.M. Blackburn, et al., *Nucleosides & Nucleotides*, 10, 549 (1991).
J.C. Baker, et al., *Mutation Res.*, 208, 87 (1988).
G. Klein, et al., *Biochemistry*, 27, 1897 (1988).
E. Castro, et al., *Br. J. Pharmacol.*, 100, 360 (1990).
D.R. Elmaleh, et al., *Proc. Natl. Acad. Sci.*, 81, 918 (1984).
R. Bone, et al., *J. Biol. Chem.*, 261, 16410 (1986).
U. Pohl, et al. *Fed Amer. Soc. Exper. Bio.*, Abstr. Part I, No. 1878 (1991).
M.T. Miras–Portugal., et al., *Ann. NY Acad. Sci.*, 603, 523 (1990).
A. Guranowski, et al., *Biochemistry*, 27, 2959 (1988).
F. Grummt, et al., *Plant Mol. Bio.*, 2, 41 (1983).
A.G. McLennan, et al., *Nucleic Acid Res.*, 12 1609 (1984).
P. Zamecnik, et al., *Analytical Biochem.*, 134, 1 (1983).
E. Rapaport, et al., *Proc. Natl. Acad. Sci.*, 78, 838 (1981).
T. Kimura, et al., *Biol. Pharm. Bull.*, 18, 1556 (1995).
E. Schulze–Lohoff, et al., *Hypertension*, 26, 899 (1995).
B.K. Kim, et al., *Proc. Natl. Acad. Sci.*, 89, 11056 (1992).
H. Morli, et al., *Eur. J. Biochem.*, 205, 979 (1992).
E. Castro, et al., *Pflugers Arch.*, 426, 524 (1994).
H. Schluter, et al., *Nature*, 367, 186, (1994).
E. Castro, et al., *Br. J. Pharmacol.*, 106, 833 (1992).
T. Casillas, et al., *Biochemstry*, 32, 14203 (1993).
J. Pintor, et al., *J. Neurochem.*, 64, 670 (1995).
E. Castro, et al., *J. Biol. Chem.*, 270, 5098 (1995).
V.A. Panchenko, et al., *Neuroscience*, 70, 353 (1996).
J. Pintor, et al., *Br. J. Pharmacol.* 115, 895 (1995).
A. Kanavarioti, et al., *Tett. Lett.*, 32, 6065 (1991).
Blaug, et al., "$P2Y_2$ Rceptor Agonists Induce Prolonged Calcium, Membrane Voltage Conductance and Fluid Absorption Increases in Bovine RPE," *IOVS* 41(4): S136 (2000) XP001088187.
Burnstock, et al. "P2 purinergic reeptors: Moduclation of cell function and therapeutic potential," *Journal of Pharmacology and Experimental Therapeutics* 295(3) 862–869 (2000) XP002208652.
Ferris, et al. "Oligomerization reactionsof deoxyribonucleotides on montmorillonite clay: the effect of mononucleotide structure on phosphodiester bond formation," *Origins Life Evol. Biosphere* 19(6): 609–619 (1989) XP001085277.
Maminishkis, et al., "Purinoceptor agonists increase fluid clearance out of subretinal space (SRS) blebs in vovo," *IOVS*, 41(4): S136 (2000) XP001083820.
Peterson, et al., "Extracellular ATP activities calcium signaling, ion, and fluid transport in retinal pigment epithelium," Journal of Neuroscience, *17*: 2324–2337 (1997) XP001087693.
Sillero, et al., "2', 3'–Dideoxynucleoside triphosphates (ddNTP) and di–2',3'–dideoxynucleoside tetraphosphates (ddNp4ddN) behave differently to the corresponding NTP and Np4N counterparts as substrates of firefly luciferase, and dinucleoside tetraphosphatase and phosphodiesterases," *Biochemica et Biophysica Acta* 1334(2–3): 191–199 (1997) XP002208651.
Theoclitou, et al. "Characterization of stress protein LysU. Enzyme synthesis of diadenosine 5',5'''–P1, P4–tetraphosphate (Ap4A) analogs by LysU, *J. Chem. Socc., Perkins Trans.*1(16) : 2009–1019 (1996) XP00108769.
Williams, "P2 Receptors as drug discovery targets," Abstract Paper *Am. Chem. Soc.* (2000) XP001085299.

\* cited by examiner

USE OF CERTAIN DINUCLEOTIDES TO STIMULATE REMOVAL OF FLUID IN RETINAL DETACHMENT AND RETINAL EDEMA

This application is a continuation-in-part of U.S. Application Ser. No. 09/101,395, filed Jul. 13, 1998, which issued as Pat. No. 6,348,589 on Feb. 19, 2002; which was the National Stage of International Application No. PCT/US98/02702, filed Feb. 6, 1998, published Aug. 13, 1998 under PCT Article 21(2) in English; and was a continuation-in-part of U.S. patent application Ser. No. 08/798,508, filed Feb. 10, 1997, which issued as Pat. No. 5,837,861 on Nov. 17, 1998. This and all other U.S. patents cited herein are specifically incorporated herein by reference in their entirety.

TECHNICAL FIELD

This invention relates to a method of treating eye disease. Specifically, this invention relates to a method of removing pathological fluid accumulation in subretinal and intra-retinal spaces, by administering P2Y receptor agonists such as certain dinucleotides to a subject in need of such a treatment. The method comprises administering metabolically stable, hydrolysis resistant P2Y receptor agonists, such as certain dinucleotides, in an amount effective to treat the family of blinding conditions comprising retinal detachment and retinal edema.

BACKGROUND OF THE INVENTION

The retinal pigment epithelium (RPE) lies in the back of the vertebrate eye and forms a barrier that separates the retina from the choroidal blood supply. A critical function of the RPE is to maintain and regulate the hydration of the subretinal space, the extracellular volume that exists between the retina and the RPE. (Marmor, pp. 3–12, in *The Retinal Pigment Epithelium,* Eds. M. F. Marmor and T. J. Wolfensberger, Oxford University Press, New York, (1998)) This function is achieved by the regulated transport of fluid, ions, and metabolites between the subretinal space and the choroidal blood supply. (Marmor, pp. 420–438, in *The Retinal Pigment Epithelium,* Eds. M.F. Marmor and T. J. Wolfensberger, Oxford University Press, New York, (1998); Pederson, pp. 1955–1968, in *Retina,* Ed. S. J. Ryan, Mosby, St. Louis, (1994)). Like all epithelia, the RPE contains two functionally and anatomically distinct membranes: an apical membrane that faces the retina, and a basolateral membrane that faces the choroidal blood supply. In the normal retina, fluid is absorbed across the RPE in the direction of the subretinal space to the choroid. This active absorption of fluid by the RPE, often referred to as the "RPE pump," plays a critical role in maintaining proper attachment of photoreceptors to the apical membrane of the RPE by pumping fluid out of the retinal spaces. (Marmor, pp. 1931–1954, in *Retina,* Ed. S. J. Ryan, Mosby, St. Louis, (1994); Hughes, et al., pp. xvii, 745, in *The Retinal Pigment Epithelium,* Eds. M.F. Marmor and T. J. Wolfensberger, Oxford University Press, New York, (1998)).

Retinal detachment is characterized by abnormal accumulation of fluid in the subretinal space leading to detachment of the retina from the underlying retinal pigment epithelium. Retinal edema refers to abnormal accumulation of fluid within the retina itself. Retinal detachment or edema in the central part of the retina (macula) produces significant loss of vision, and can ultimately lead to irreversible blindness. (Yanoff and Duker, Ophthalmology, Mosby, Philadelphia, (1999); Wilkinson, et al., *Michels's Retinal Detachment,* 2nd ed. Mosby, St. Louis, (1997)) A wide variety of ocular pathologies can result in retinal detachment or retinal edema. The most common type of retinal detachment is rhegmatogenous retinal detachment, which occurs as a result of single or multiple tears or holes in the retina that permit liquefied vitreous to enter into the subretinal space and create a retinal detachment.

There are no pharmacological approaches employed in the treatment of rhegmatogenous retinal detachment (RRD). The only current treatments for RRD are surgical (scleral buckling, pneumatic retinopexy, or vitrectomy). (Wilkinson, et al., *Michels's Retinal Detachment,* 2nd ed., Mosby, St. Louis, (1997)). There are two vital components for successful RRD surgery: reattachment of the retina and repair of the retinal break. The principal difference among the three surgical techniques for treating RRD is in the method employed to facilitate retinal reattachment.

Scleral buckle uses an extraocular buckle (usually a silicone sponge or solid silicone) that is sewn to the sclera towards the detached retina (Wilkinson, et al, *Michels's Retinal Detachment,* 2nd ed., Mosby, St. Louis (1997)) The retina usually reattaches over a period of a few days, but may take up to a few weeks. The surgeon may elect to drain the subretinal fluid at the time of operation by inserting a needle through the sclera, choroid, and RPE. In general, the buckle remains permanently sewn to the sclera. In pneumatic retinopexy, a gas bubble is injected directly into the vitreous, and the head is positioned so that the gas bubble acts as a tamponade and covers the retinal break. (Tornambe and Hilton, *Ophthalmology* 96(6): 772–83 (1989)). The subretinal fluid usually resolves within 1–2 days, but precise head positioning is required to insure that the bubble covers the retinal break. (Tornambe, et al., *Am. J. Ophthalmol.* 127(6): 741–3 (1999)). Vitrectomy is usually used for complex RRD associated with vitreous traction or hemorrhage, but is occasionally used for simple RRD (Chang, pp. 8.34.1–8.34.6, in *Ophthalmology,* Eds. M. Yanoff and J. S. Duker, Mosby, Philadelphia, (1999)). The procedure involves making three small incisions through the sclera to allow the introduction of instruments in the vitreous cavity. The vitreous is removed and replaced with a special saline solution. Depending on the type and cause of the detachment, a variety of instruments and techniques are then used to reattach the retina. For simple detachments, the retina is flattened via anterior drainage of the subretinal space by insertion of needle through the retinal tear.

Scleral buckle and vitrectomy often require general anesthesia and can involve hospitalization. Pneumatic retinopexy is usually done in the physician's office, but requires patient compliance for success. (Hilton and Tornambe, *Retina* 11(3): 285–94 (1991); Hilton and Brinton, pp. 2093–2112, in *Retina,* Ed. Stephen J. Ryan, Mosby, Philadelphia, (1999); Han, et al., *Am. J. Ophthalmol.* 126(5): 658–68 (1998)). Depending on the surgical technique and the surgeon, success rates can vary following single surgery, with lower rates for pneumatic retinopexy and higher rates for scleral buckle. (Tornambe, et al., *Am. J. Ophthalmol.* 127(6): 741–3 (1999); Han, et al., *Am. J. Ophthalmol.* 126(5): 658–68 (1998)) The success of retinal detachment surgery is measured in terms of retinal reattachment at any point following surgery (ranging from hours to weeks). Parameters such as visual outcome and patient quality-of-life are not used to assess success of retinal detachment surgery.

The conditions that are commonly associated with the more severe formns of intra-retina edema are diabetic macular edema, exudative age-related macular degeneration (AMD) and clinically significant cystoid macular edema.

(Jampol and Po, pp. 999–1008, in *Retina*, Ed. S. J. Ryan, Mosby, St. Louis, (1994)) Other pathological conditions associated abnormal fluid accumulation in intra-retinal or subretinal spaces include uveitis, central and branch vein occlusion, retinitis pigmentosa, central serous retinopathy, CMV retinitis, and choroidal melanoma. Physical trauma associated with ocular injury following certain surgical procedures (such as cataract surgery) can also produce retinal detachment or edema. (Ahmed and Ai, pp. 8.34.1–8.34.6, in *Ophthalmology*, , Eds. M. Yanoff and J. Duker, Mosby, Philadelphia, (1999)).

Intra-retina accumulation of fluid in the macula results in decreased visual acuity and is the most common cause of vision loss in patients with diabetic retinopathy, AMD and other ischemic retinopathies such as branch and central retinal vein occlusion. (Jampol and Po, pp. 999–1008, in *Retina*, Ed. Stephen J. Ryan, Mosby, St. Louis, (1994); Kent, et al., *Br. J. Ophthalmol.* 84(5): 542–5 (2000)). Macular edema is a frequent complication of uveitis and is commonly seen in patients with retinitis pigmentosa. (Rothova, et al., *Br. J. Ophthalmol.* 80(4): 332–6 (1996); Fetkenhour, et al., *Trans. Am. Acad. Ophthalmol. Otolaryngol.* 83(3) Pt 1: OP515–21 (1977)) Macular edema is also a major cause of decreased vision following intraocular surgery (called cystoid macular edema). (Miyake, *Surv. Ophthalmol.* 28 Suppl: 554–68 (1984)) Accumulation of intra-retina fluid is believed to result from a breakdown of the inner and/or outer blood-retinal barrier. (Kent, et al., *Br. J. Ophthalmol.* 84(5): 542–5 (2000)) The inner retinal barrier consists of endothelial cells of the retinal vasculature and the outer barrier comprises of the retinal pigment epithelium. Breakdown of the blood-retinal barrier can result in focal leakage of fluid from the vasculature and fluid accumulation within retinal layers or in the subretinal space. The present treatments for retinal edema include systemic and topical administrations of corticosteroid, acetazolamide, and non-steroidal anti-inflammatory drugs, as well as surgical options such as vitrectomy, grid, and focal laser photocoagulation. These therapies show limited utility in patients. The present invention discloses significant improvements in the treatment of retinal edema.

Although modern day RRD surgery has a relatively high success rate (60–90%), it is thought that a pharmaceutical composition that can reattach the retina in cases where surgery failed would be of enormous patient benefit. In addition, if the pharmaceutical composition can reattach the retina in the absence of surgical intervention, it would be most therapeutically useful, particularly in the treatment of rhegmatogenous retinal detachment. The present invention discloses pharmaceutical compositions and methods of use thereof that will significantly improve upon existing treatments for retinal detachment.

A number of pharmacological and surgical approaches are employed to treat cystoid and diabetic macular edema, but they are generally considered empirical and often ineffective. Non-specific anti-inflammatory treatment is used for all types of macular edema, except in cases associated with ischemic retinopathies in which laser treatment is indicated (Kent, et al., *Br. J. Ophthalmol.* 84 (5): 542–5 (2000)). Corticosteroids are frequently used to treat macular edema, but were shown to be ineffective in a randomized, placebo controlled study (Flach, et al., *Am. J. OphthalmoL.* 103(4): 479–86 (1987); Flach, et al., *Ophthalmology*, 97(10): 1253–8 (1990)). Acetazolamide also alleviates certain types of macular edema and is postulated to work via activation of the RPE pump, but systemic tolerance to acetazolamide is poor. (Cox, et al., *Arch. Ophthalmol.* 106(9):1190–5 (1988)).

Focal or grid laser photocoagulation is commonly used to reduce retinal vascular leakage associated with diabetic retinopathy, and is useful in limited cases. ( Ip, et al., *In Ophthalmology*, London; Philadelphia: Mosby, 8.4.1–8.4.2 (1999); The Diabetic Retinopathy Study Research Group, *Ophthalmology* 88 (7): 583–600 (1981); Early Treatment Diabetic Retinopathy Study Research Group, *Arch. Ophthalmol.* 103(12): 1796–806 (1985); The Branch Vein Occlusion Study Group, *Am. J. Ophthalmol.* 98(3): 271–82 (1984)). In addition, vitrectomy is employed to treat diabetic retinopathies associated with vitreal hemorrhages and/or vitreoretinal traction.(Wilkinson, et al, *Michels's Retinal Detachment*, 2nd ed., Mosby, St. Louis, (1997)). There remains a large unmet medical need for a safe, effective treatment of macular edema. (Kent, et al., *Br. J. Ophthalmol.* 84(5): 542–5 (2000)) The present invention provides significant improvement to patients that suffer from retinal and macular edema.

Previous work has shown that the apical (retinal-facing) membrane of the RPE contains P2Y receptors that can be activated to stimulate fluid transport across the RPE in the direction of the subretinal space to the choroidal blood supply, and this mechanism of action was proposed to facilitate the removal of subretinal fluid in retinal detachment. (Peterson, et al, *J. Neurosci.* 17(7): 2324–37 (1997)) However, the natural ligands for the $P2Y_2$ receptor are ATP and UTP, both of which are rapidly degraded by ubiquitous extracellular nucleotidases. Therefore, in order for ATP and UTP to be efficacious in the treatment of retinal detachment, these compounds need to be delivered directly into the subretinal space. However, drug delivery into the subretinal space is widely regarded to be unacceptably risky for patients because it involves the insertion of a needle between the retina and RPE, which can result in complications and blindness. Therefore, in order for ATP or UTP to be therapeutically useful, it must be delivered into the intravitreal cavity, which is a much less invasive procedure. However, in order for ATP or UTP to reach the RPE apical membrane, it must diffuse across the retina. The retina is a 200–300 $\mu$m thick layer of neuronal, glial, and endothelial tissue, and is one of the most metabolically active tissues in the body when normalized by tissue weight. ATP and UTP are expected to be completely degraded during their diffusion through the retinal layers. The present invention overcomes this limitation by disclosing novel hydrolysis-resistant agonists of the P2Y receptor that are efficacious when delivered into the vitreous, and methods of using such agonists in the treatment of retinal detachment and edema.

SUMMARY OF THE INVENTION

Pharmaceutical compositions and methods of use thereof for stimulating removal of extraneous fluid in the retina or subretinal space in a subject in need of such treatment are disclosed. The methods and compositions disclosed in the present invention may be used to stimulate removal of extraneous intra-retinal or subretinal fluid for any reason, including, but not limited to, primary and adjunctive treatments of rhegmatogenous retinal detachment, serous retinal detachment, all forms of cystoid macular edema (uveitis, post-surgical, central and branch vein occlusion, and inherited retinal diseases such as retinitis pigmentosa), and all forms of retinal and macular edema (proliferative and non-proliferative, exudative age-related macular degeneration, and retinopathy of prematurity.)

The present invention discloses methods of treating a subject with retinal detachment or retinal edema by administering pharmaceutical composition according to Formulae I, Ia and Ib via intravitreal injection, intravitreal sustained release or delivery, ocular surface instillation, transcleral injection or infusion, or systemic injection or infusion. The present invention also discloses aqueous, gel, gel-like, and solid formulations for pharmaceutical compositions. A preferred embodiment consisting of a pharmaceutical composition for acute or chronic use in the treatment of retinal detachment and retinal edema is also disclosed.

The method comprises administration to a subject an effective dose of a pharmaceutical composition comprising a P2Y receptor ligand with or without therapeutic and adjuvant agents commonly used to treat or manage retinal detachment. An effective dose of the composition is that amount which activates P2Y receptors and facilitates outflow of fluid, sufficient to effectuate removal of extraneous fluid from the retina or subretinal space. Although $P2Y_2$ receptor agonists are optimally effective in facilitating the removal of extraneous retinal or subretinal fluids, agonists of other P2Y receptor subtypes, specifically $P2Y_1$, $P2Y_4$, $P2Y_6$, and $P2Y_{11}$, are also effective.

The pharmaceutical compositions useful in this invention comprise $P2Y_2$ receptor agonists, including certain adenine-, uridine-, and cytidine-containing dinucleotides. Such pharmaceutical compounds include dinucleotide analogues, which are selective agonists of the P2Y receptor on epithelial cells of the retinal pigment epithelium. Activation of P2Y receptors by such agonists is associated with elevated intracellular calcium levels and increased fluid transport across the RPE.

DETAILED DESCRIPTION OF THE INVENTION

The present invention provides a method of increasing fluid absorption across the retinal pigment epithelium (RPE) to facilitate the removal of extraneous intra-retinal or subretinal fluid from the posterior portion of the eye to treat diseases that lead to retinal detachment and retinal edema. The method comprises administration of an effective dose of the P2Y receptor agonist with or without therapeutic and adjuvant agents commonly used to treat or manage retinal detachment and retinal edema. An effective dose will be the amount of such agonist necessary to activate P2Y receptors at the retinal-facing (apical) membrane of retinal pigment epithelial cells and to enhance fluid absorption (retinal-to-choroidal direction) across the RPE. The present invention relates to a novel approach for stimulating the removal of extraneous fluid from the retina and subretinal spaces, and thus can be useful in the prevention, management and treatment of disorders associated with retinal detachment and retinal edema.

The method of the present invention is useful for the management and/or treatment of all disorders associated with retinal detachment and retinal edema, including but not limited to rhegmatogenous retinal detachment, serous retinal detachment, all forms of cystoid macular edema (uveitis, post-surgical, central and branch vein occlusion, and inherited retinal diseases such as retinitis *pigmentosa*), and all forms of retinal and macular edema (proliferative and non-proliferative diabetic macular edema, exudative age-related macular degeneration, and retinopathy of prematurity).

The method of the present invention is useful to enhance the effects of surgery, pharmacotherapy, and adjunctive agents used to treat and manage disorders associated with retinal detachment and retinal edema. Surgical approaches include scleral buckle, pneumatic retinopexy, macular translocation and vitrectomy. Pharmacotherapeutic agents such as corticosteroids and acetazolamide have been used to manage macular edema.

High doses may be required for some therapeutic agents to achieve levels to effectuate the target response, but may often be associated with a greater frequency of dose-related adverse effects. Thus, combined use of the compounds of the present invention with agents commonly used to treat retinal detachment and retinal edema permits relatively lower doses of such agents resulting in a lower frequency of adverse side effects associated with long-term administration of such therapeutic agents. Thus, another indication of the compounds in this invention is to reduce adverse side effects of drugs used to treat retinal detachment and retinal edema, such as the development of systemic effects with acetazolamide.

DESCRIPTION OF COMPOUNDS

This invention provides a method of using a pharmaceutical composition comprising P2Y receptor agonists for removing pathological fluid accumulation in subretinal and intra-retinal spaces, and thereby treating edematous retinal disorders, including retinal detachment and retinal edema. P2Y receptor agonists include dinucleotides and their analogues, which activate $P2Y_1$, $P2Y_2$, $P2Y_4$, $P2Y_6$, and $P2Y_{11}$, and most preferably $P2Y_2$ receptors. Dinucleoside polyphosphates of general Formula I are also useful in this application.

Accordingly, a broad embodiment of the invention is directed to compounds of general Formula I or the pharmaceutically acceptable non-toxic salts thereof:

Formula I wherein:
X is oxygen, methylene, difluoromethylene, or imido;
n=0, 1 or 2;
m=0, 1 or 2;
n+m=0, 1, 2, 3 or 4;
Z=OH or H;
Z'=OH or H;
Y=H or OH;
Y'=H or OH; and
B and B' are each independently a purine residue or a pyrimidine residue, as defined in Formula Ia and Ib, respectively, linked through the 9- or 1-position, respectively.

Formula Ia wherein:
$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;
$R_2$ is hydroxy, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino (wherein alkyl groups are optionally linked to $N_7$ to form a substitute ring), acylamino, diacylamino, or $NHR_y$;
$R_x$ is O (adenine 1-oxide derivatives), or is absent (adenine derivatives);
wherein $R_2$ is $NHR_y$, and $R_y$ and $R_x$ taken together form a 5-membered fused imidazole ring (1, $N^6$-ethenoadenine derivatives), optionally substituted on the 4- or 5-positions of the etheno moiety with alkyl, aryl or aralkyl moieties as defined below;
$R_3$ is hydrogen, azido, alkoxy, aryloxy, aralkyloxy, alkylthio, arylthio, or aralkylthio as defined below; or A($C_{1-6}$alkyl)OCONH($C_{1-6}$alkyl)B- wherein A and B are independently amino, mercapto, hydroxy or carboxyl; or pharmaceutically acceptable esters, amides or salts thereof.
Thus, the substituted derivatives of adenine include adenine 1-oxide; 1,$N^6$-(4-or 5-substituted etheno) adenine; 6-substituted adenine; or 8-substituted aminoadenine, where R' of the 6- or 8-HNR' groups are chosen from among: arylalkyl ($C_{1-6}$) groups with the aryl moiety optionally functionalized as described below; alkyl; and alkyl groups with functional groups therein, such as: ([6-aminohexyl] carbamoylmethyl)-, and ω-acylated- amino(hydroxy, thiol and carboxy)alkyl($C_{2-10}$)- and their ω-acylated-amino (hydroxy, thiol and carboxy) derivatives where the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$ alkyl group.
J is carbon or nitrogen, with the provision that when J is nitrogen, $R_3$ is not present;
wherein the alkyls are straight-chain, branched or cyclic;
wherein the aryl groups are optionally substituted with lower alkyl, amino, alkylamino, $NO_2$, $N_3$, carboxylic, amido, sulfonamido, or halo groups; and
B and B', can also be a pyrimidine with the general formula of Formula Ib, linked through the 1- position to a ribosyl residue:

Formula Ib wherein:
$R_4$ is hydrogen, hydroxy, oxo, mercapto, amino, cyano, $C_{7-12}$arylalkoxy, $C_{1-6}$ alkylthio, $C_{1-6}$ alkoxy, $C_{1-6}$ alkylamino, or di$C_{1-4}$alkylamino, wherein the alkyl groups are optionally linked to form a heterocycle;
$R_5$ is hydrogen, acetyl, benzoyl, $C_{1-6}$ alkyl, $C_{1-5}$ alkanoyl, aroyl, or absent;
$R_6$ is hydroxy, oxo, mercapto, $C_{1-4}$alkoxy, $C_{7-12}$arylalkoxy, $C_{1-6}$alkylthio, amino, S-phenyl, $C_{1-5}$ disubstituted amino, triazolyl, $C_{1-6}$alkylamino, or di-$C_{1-4}$alkylamino, wherein said dialkyl groups are optionally linked to form a heterocycle or linked to $N^3$ to form a substituted ring; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{14}$ alkylamino, and di- $C_{1-4}$ alkylamino, wherein said dialkyl groups are optionally linked to form a heterocycle;
$R_7$ is selected from the group consisting of: hydrogen, hydroxy, cyano, nitro, and $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with a substituent selected from the group consisting of: $C_{1-6}$ alkyl or phenyl; substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5 or 6-membered saturated or unsaturated ring bonded through N or O or S at $R_6$, such ring optionally contains substituents that themselves contain functionalities; provided that when $R_8$ is amino or substituted amino, $R_7$ is hydrogen; and $R_8$ is selected from the group consisting of: hydrogen, amino or di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, and phenylthio.

The ribosyl moieties are in the D-configuration, as shown, but may be L-, or D- and L-. The D-configuration is preferred. The nucleoside residues include the sugar moieties ribofuranosyl, arabinofuranosyl, 2'-deoxyribofuranosyl, 3'-deoxyribofuranosyl, xylofuranosyl, and lyxofuranosyl; and can be in the alpha- or beta- and D- or L-configurations, but most preferably the beta-D-configuration.

In the general structure of Formulae I, Ia and Ib above, the dotted lines in the 2- to 6- positions are intended to indicate the presence of single or double bonds in these positions; the relative positions of the double or single bonds being determined by whether the $R_4$, $R_5$ and $R_6$ substituents are capable of keto-enol tautomerism.

In the general structures of Formula I above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl alkenyl, alkynyl, and aryl groups are selected from halogen, hydroxy, $C_{1-4}$ alkoxy, $C_{1-4}$ alkyl, $C_{6-12}$aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

Compounds encompassed by the present invention may be prepared by condensation of a nucleoside mono-, di-, or triphosphate, activated with a condensing agent such as, but not limited to, carbonyldiimidazole or dicyclohexylcarbodiimide, with a second molecule of the same or a different mono-, di-, or triphosphate to form the desired dinucleoside polyphosphate. Another method of preparation is the sequential condensation of a nucleoside phosphate, activated as above, with a non-nucleoside mono-, di- or polyphosphate moiety, such as, but not limited to, a monophosphate or pyrophosphate anion to yield the desired dinucleoside polyphosphate, the non-isolated intermediate in such a case being a mononucleotide polyphosphate. Yet another preparative approach is the sequential condensation of a mono-, di- or polyphosphate moiety, activated as mentioned above, or in the form of an acid halide or other derivative reactive toward nucleophilic displacement, with a nucleoside phosphate or polyphosphate to yield the desired dinucleoside polyphosphate. The desired dinucleoside polyphosphate may be formed by modification of a pre-formed dinucleoside polyphosphate by substitution or derivatization of a moiety or moieties on the purine, pyrimidine or carbohydrate ring. Nucleoside phosphates used as starting materials may be commercially available, or may be made from the corresponding nucleosides by methods well known to those skilled in the art. Likewise, where nucleosides are not commercially available, they may be made by modification of other readily available nucleosides, or by synthesis from heterocyclic and carbohydrate precursors by methods well known to those skilled in the art (International Patent Nos. WO 96/40059, WO 96/02554A1, WO-A-9815563, and WO 98/55494; Theoclitou, et al., J. Chem. Soc. Perkin Trans. I, 2009–2019 (1996); Guranowski, et al., *Nucleosides and Nucleotides* 14, 731–734 (1995); Visscher, et al., *Nucleic Acids Research* 20, 5749–5752 (1992); Holler, et al, *Biochemistry* 22, 4924–4933 (1983); Orr, et al., *Biochem. Pharmacol.* 673–677 (1988); Plateau, et al., *Biochemistry* 24, 914–922 (1985); Hagmeier, et al., *J. Chromatography* 237, 174–177 (1982); Scheffzek, et al., *Biochemistry* 35, 9716–9727 (1996); Stridh, et al., *Antiviral Res.,* 97–105 (1981); Tarasova, et al., *Chem. Abs.* 110, 154770 (1988); Hata, et al., *Chem Lett.,* 987–990 (1976); Huhn, et al., 28, 1959–1970 (1993); Tumanov, et al., *Chem. Abs.* 109–6867d (1987); Pintor, et al., *Molecular Pharmacology* 51, 277–284 (1997); and U.S. Pat. Nos. 4,855,304; 5,635,160; 5,495,550; and 5,681,823).

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general, the need for such protecting groups will be apparent to those skilled in the art of organic synthesis as well as the conditions necessary to attach and remove such groups.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$(wherein X is $C_{1-4}$). Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies, which may be employed to prepare non-toxic pharmaceutically acceptable salts and acylated prodrugs of the compounds.

Though the compounds of the present invention are primarily concerned with the treatment of human subjects, they may also be employed for the treatment of other mammalian subjects such as dogs and cats for veterinary purposes.

The pharmaceutical utility of compounds of this invention is indicated by the inositol phosphate assay for $P2Y_2$ and other P2Y receptor activity. This widely used assay, as described in Lazarowski, et al. (1995) (*Brit. J. Pharm.* 116, 1619–27), relies on the measurement of inositol phosphate formation as a measurement of activity of compounds activating receptors linked via G-proteins to phospholipase C.

The efficacy of these compounds is reflected in their ability to facilitate removal of pathological fluid accumulation in the sub-retinal and intra-retinal spaces, associated with edematous retinal disorders including retinal detachment and retinal edema. The effective dose will depend on characteristics of the individual patient, activity of the specific compound employed, mode of administration, and characteristics of the disease or disorder, and can be determined by those skilled in the art.

Dosage levels to remove extraneous fluid within intraretinal or subretinal spaces are of the range of 10 µg/eye to 10 mg/eye, preferably in the range 50 µg/eye to 6 mg/eye, and most preferably 0.1 mg/eye to 4 mg/eye.

ADMINISTRATION OF COMPOUNDS

The active compounds disclosed herein may be administered to the eyes of a patient by any suitable means, but are preferably administered by administering a liquid or gel suspension of the active compound in the form of drops, spray or gel. Alternatively, the active compounds may be applied to the eye via liposomes. Further, the active compounds may be infused into the tear film via a pump-catheter system. Another embodiment of the present invention involves the active compound contained within a continuous or selective-release device, for example, membranes such as, but not limited to, those employed in the Ocusert® System (Alza Corp., Palo Alto, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lachrymal tissues or onto the eye surface.

The active compounds disclosed herein are preferably administered by administering an aqueous suspension into the vitreous. Intravitreal administration comprising: single or multiple intravitreal injections; administration directly into the vitreal chamber during surgery separately or in conjunction with intraocular irrigation solutions, or other similar solutions or devices, routinely used during vitreoretinal surgery; administration via liposomes or other suitable pharmaceutical carriers; administration via continuous or selective-release intravitreal-implantable devices, including, but not limited to, Ocusert® (Alza Corp., Palo Alto, Calif.) and Vitrasert (Bausch and Lomb, Inc., Rochester, N.Y.). The intravitreal solution containing the active compound may contain a physiologically compatible vehicle, as those skilled in the ophthalmic art can select using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride. The preferred embodiment is an intravitreal solution comprising active compound and saline at neutral pH and physiological osmolarity.

The topical solution containing the active compound may also contain a physiologically compatible vehicle, as those skilled in the ophthalmic art can select using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound would be absorbed into the bloodstream via the lungs or contact the ocular tissues via the nasolacrimal ducts, and subsequently contact the retinal pigment epithelial cells in a pharmnaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of: of sweetening agents, flavoring agents, coloring agents and preserving agents in order to provide pharmaceutically elegant and palatable preparations. Tablets contain the active ingredient in admixture with nontoxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, or liquid suspension form of a therapeutically effective amount of the active compound.

The invention is illustrated further by the following examples, which are not to be construed as limiting the invention in scope or spirit to the specific procedures described in them.

EXAMPLE 1

Localization of P2Y$_2$-Receptor mRNA in Retina and RPE

Figure 1:
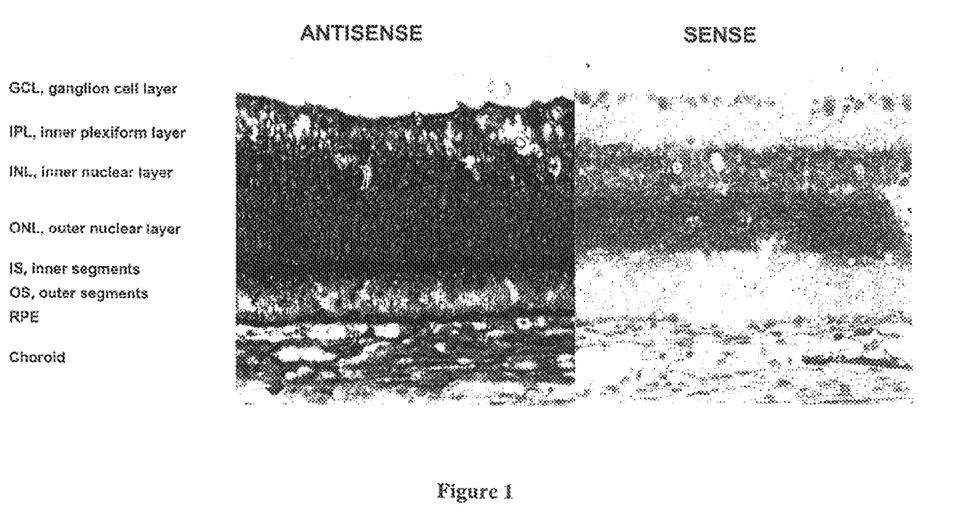
FIG. 1 represents cellular localization of $P2Y_2$ receptor mRNA in fresh frozen cross sections of albino rabbit retina/RPE/choroid tissue using nonisotopic in situ hybridization techniques. Specifically, a representative in situ hybridization result from antisense and sense digoxigenin (DIG)-labeled riboprobes engineered based on the $P2Y_2$ receptor mRNA sequence is shown.

Cellular localization of P2Y$_2$-receptor mRNA in fresh frozen cross-sections of albino rabbit retina/RPE/choroid tissue was investigated by using nonisotopic in situ hybridization techniques. FIG. 1 shows a representative in situ hybridization result from antisense and sense digoxigenin (DIG)-labeled riboprobes engineered based on the P2Y$_2$ receptor mRNA sequence. Hybridization of antisense and sense riboprobes was visualized by immunohistochemistry using alkaline phosphatase-conjugated anti-DIG antibody, and DIG-specific signal was detected using a chromophore reaction against the alkaline phosphatase, yielding purple/black staining. The tissues were also counterstained with nuclear fast red. The control sense probe (right) shows no specific labeling. Labeling with the anti-sense probe showed P2Y$_2$ receptor MRNA localization in scattered nuclei in the ganglion cell and inner nuclear layers and through the inner segment layer of photoreceptors. Strong labeling throughout the RPE was also detected, and in endothelial cells of the choroidal blood vessels.

EXAMPLE 2

Effects of Synthetic P2Y$_2$ Agonist UP$_4$dC (INS37217) on Cloned Human P2Y$_2$ Receptors The dinucleotide [P$^1$-(uridine 5'-)-P$^4$-(2'-deoxycytidine 5'-) tetraphosphate tetrasodium salt] (UP$_4$dC), also known as INS37217, was tested for its activity (potency, efficacy, and selectivity) at cloned human P2Y receptor subtypes, which were stably expressed in 1321N1 astrocytoma cells. Activity was assessed using two in vitro indices of cell activation: 1) mobilization of intracellular calcium stores, and 2) accumulation of [$^3$H]-inositol phosphates ([$^3$H]-IP). UP$_4$dC was evaluated for activity in both assays against cells expressing the P2Y$_1$, P2Y$_2$, P2Y$_4$, or P2Y$_6$ receptors.

Figure 2:
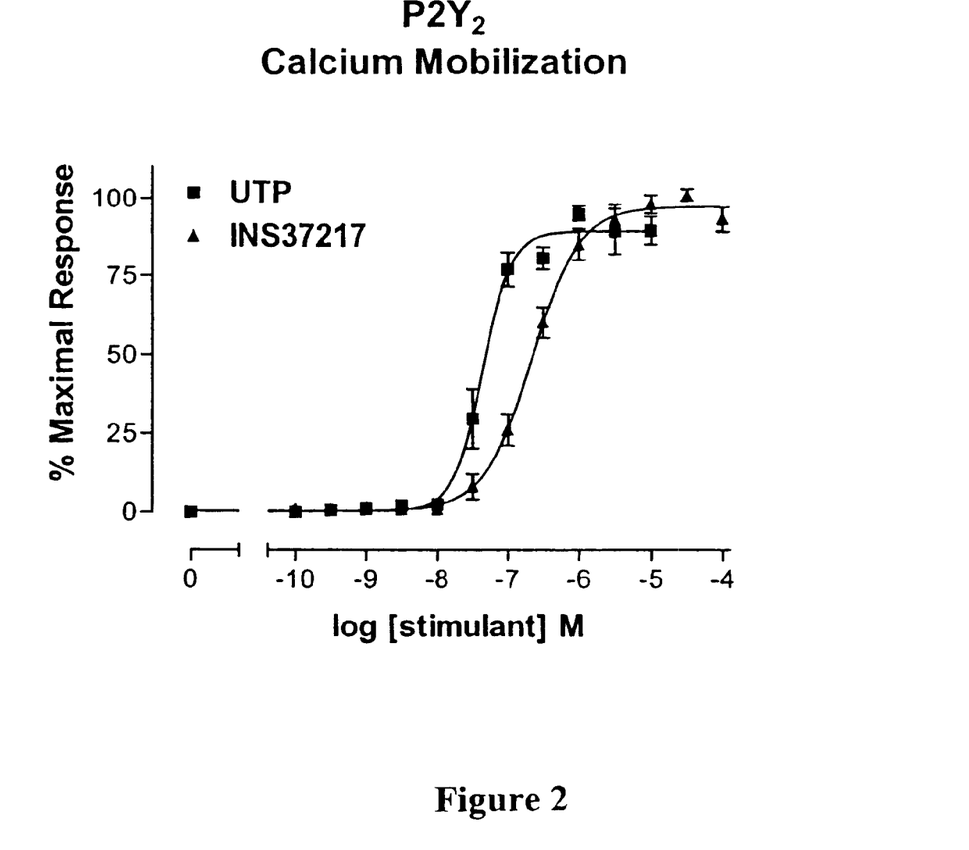
FIG. 2 represents the effects of INS37217 ($UP_4dC$) versus UTP on cytosolic calcium mobilization in 1321N1 cells overexpressing $P2Y_2$ receptor.

UP$_4$dC induced mobilization of cytosolic calcium in 1321N1 astrocytoma cells expressing human P2Y$_2$ (FIG. 2) receptors with EC$_{50}$ values of 0.22 $\mu$M and 0.8 $\mu$M, respectively. The calcium response to 100 $\mu$M UP$_4$dC was 100% of the maximal response to UTP at P2Y$_2$ receptors. In conclusion, UP$_4$dC is a full agonist for calcium mobilization at P2Y$_2$ receptors compared to UTP.

Figure 3:
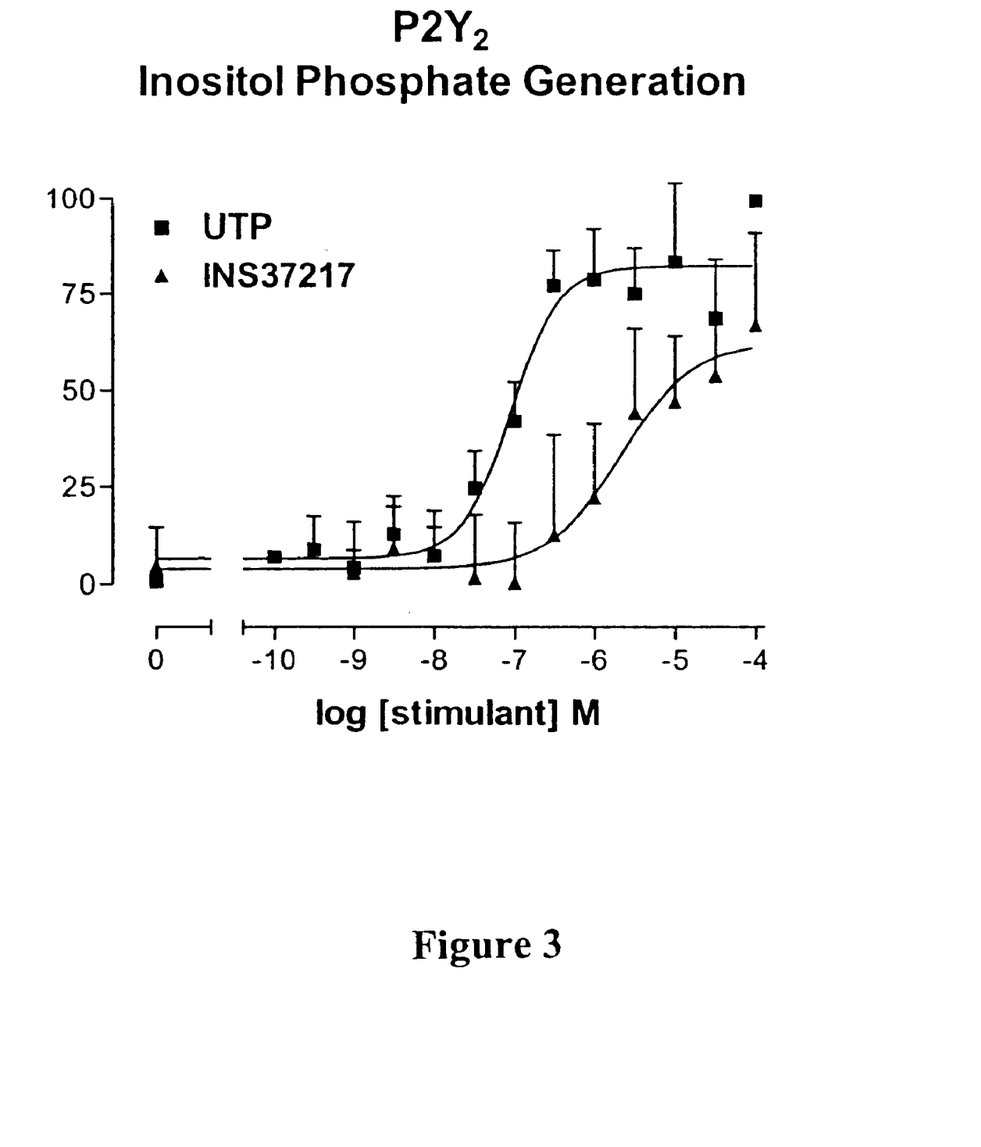
FIG. 3 represents the effect of INS37217 ($UP_4dC$) versus UTP on inositol phosphate generation in 1321N1 cells overexpressing $P2Y_2$ receptor.

UP$_4$dC stimulated [$^3$H]-IP accumulation in 1321N1 cells expressing human P2Y$_2$ (FIG. 3) receptors with an EC$_{50}$ value of 2.2 $\mu$M. The inositol phosphate response to 100 $\mu$M UP$_4$dC was approximately that of the maximal response to UTP. In conclusion, UP$_4$dC is a full agonist for inositol phosphate release at P2Y$_2$ receptors compared to UTP in the test system.

EXAMPLE 3

UP$_4$dC (INS37217) Stimulates Fluid Absorption in Freshly Isolated RPE Monolayers Fluid transport across freshly isolated, intact bovine and human fetal RPE monolayers was studied using a modified capacitance probe technique (Frambach, et al., *Biophys. J.* 47(4): 547–52 (1985); Hughes, et al., *J. Gen. Physiol.* 83(6): 875–99 (1984)).

The RPE was mounted vertically in a modified Ussing chamber such that apical and basolateral membranes were separately exposed to Ringer's solutions held in bathing reservoirs. Stainless steel capacitive probes were lowered into the apical and basolateral bathing reservoirs to sense the capacitance of the air gap between the probe and fluid meniscus. Fluid transport rate $J_v$ ($\mu$L·cm$^{-2}$·hr$^{-1}$) was determined by monitoring fluid movement-induced changes in the air gap capacitance at the apical and basolateral baths.

Figure 4:
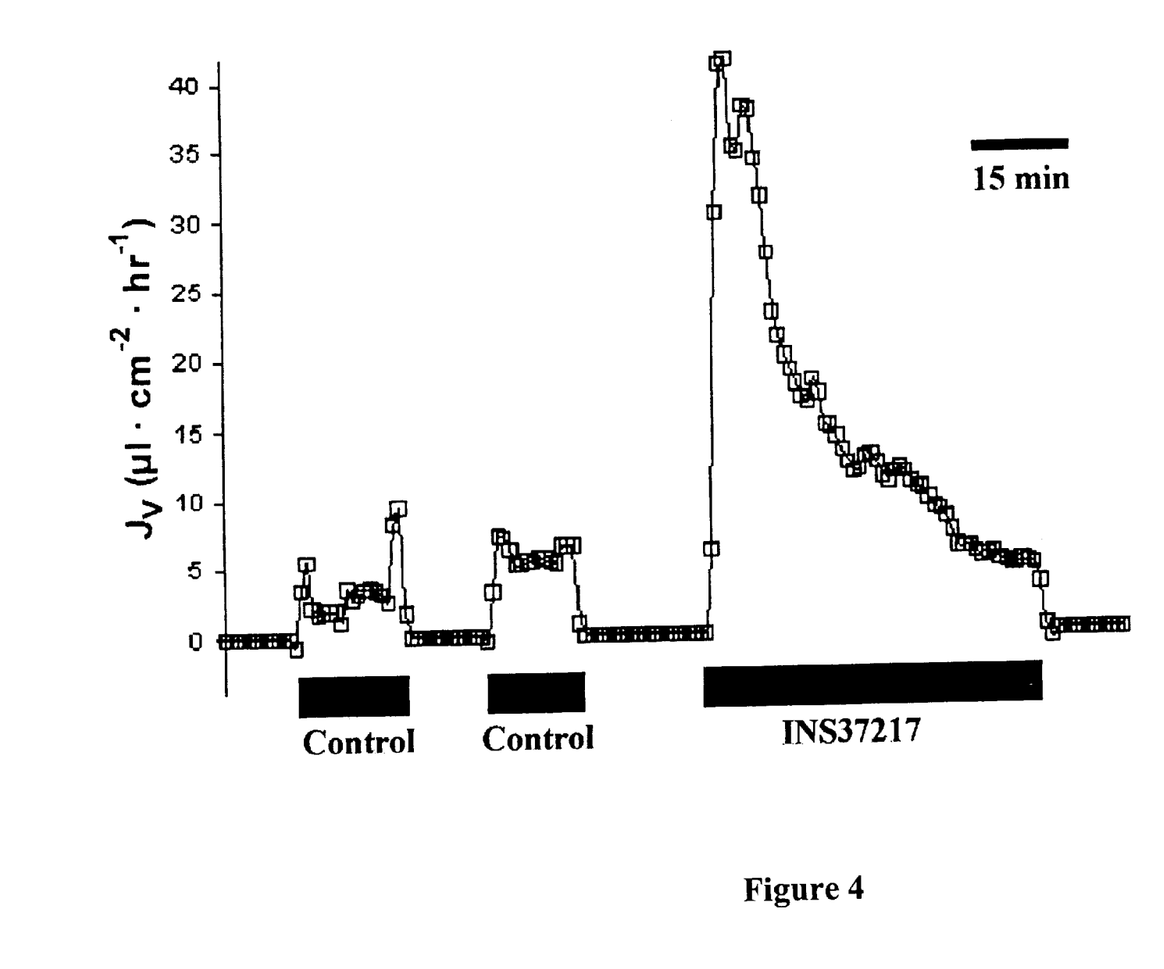
FIG. 4 represents the effects of INS37217 ($UP_4dC$) on fluid absorption in human fetal RPE.

Representative effects of agonist on $J_v$ in human fetal RPE are shown in FIG. 4. Positive $J_v$ values reflect fluid absorption (apical-to-basolateral) and negative $J_v$ values reflect fluid secretion (basolateral-to-apical). In the experiment shown in FIG. 4, control fluid movement across the freshly isolated human fetal RPE monolayer is absorptive at a rate of ~5 $\mu$L·cm$^{-2}$·hr$^1$. The addition of 50 $\mu$M agonist to Ringer's solution bathing the apical membrane elicited a transient increase in fluid absorption to ~40 $\mu$L·cm$^{-2}$·hr$^{-1}$ before returning back to pre-stimulated levels. During the 1-hour treatment period, UP$_4$dC (INS37217) increased total fluid absorption by approximately a factor of three.

Figure 5:
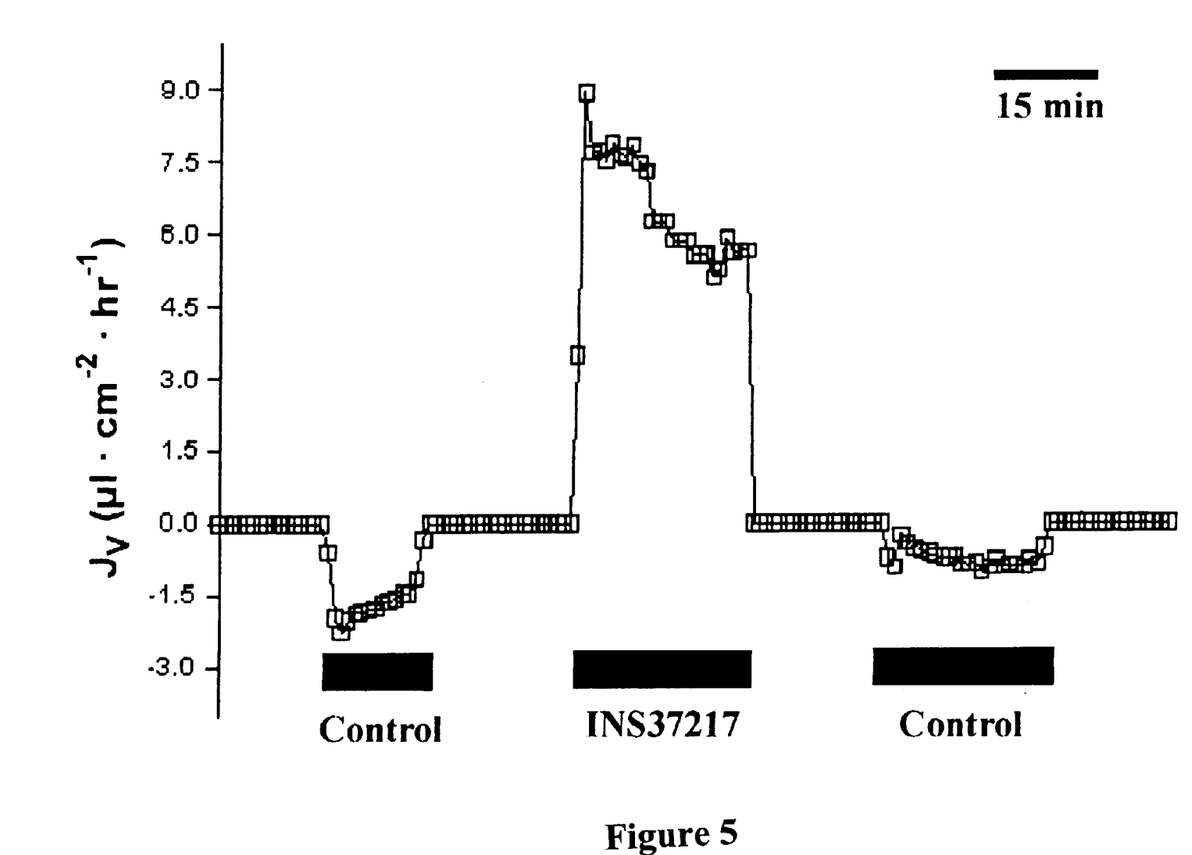
FIG. 5 represents the effects of INS37217 ($UP_4dC$) on the magnitude and direction of fluid transport in bovine RPE.

Although the RPE is normally a fluid-absorbing epithelium, fluid secretion has occasionally been observed in freshly isolated RPE preparations. It has been postulated that fluid secretion in vivo may be a normal component of RPE physiology under certain conditions, such as following a transition between dark and light, or under pathological conditions, such as in serous retinal detachments. FIG. 5 shows that in a freshly isolated bovine RPE monolayer in which $J_v$ secretion is observed under control conditions, the agonist can reverse the direction of fluid transport to absorption. The effects of agonist are reversible upon returning to control Ringer's solution. Such an effect of agonist in vivo will offer therapeutic potential in the treatment of serous retinal detachments, such as central serous retinopathy, in which abnormal RPE-mediated fluid secretion is postulated to mediate the effects of transport of choroidal fluid into the subretinal space.

EXAMPLE 4

Figure 6:
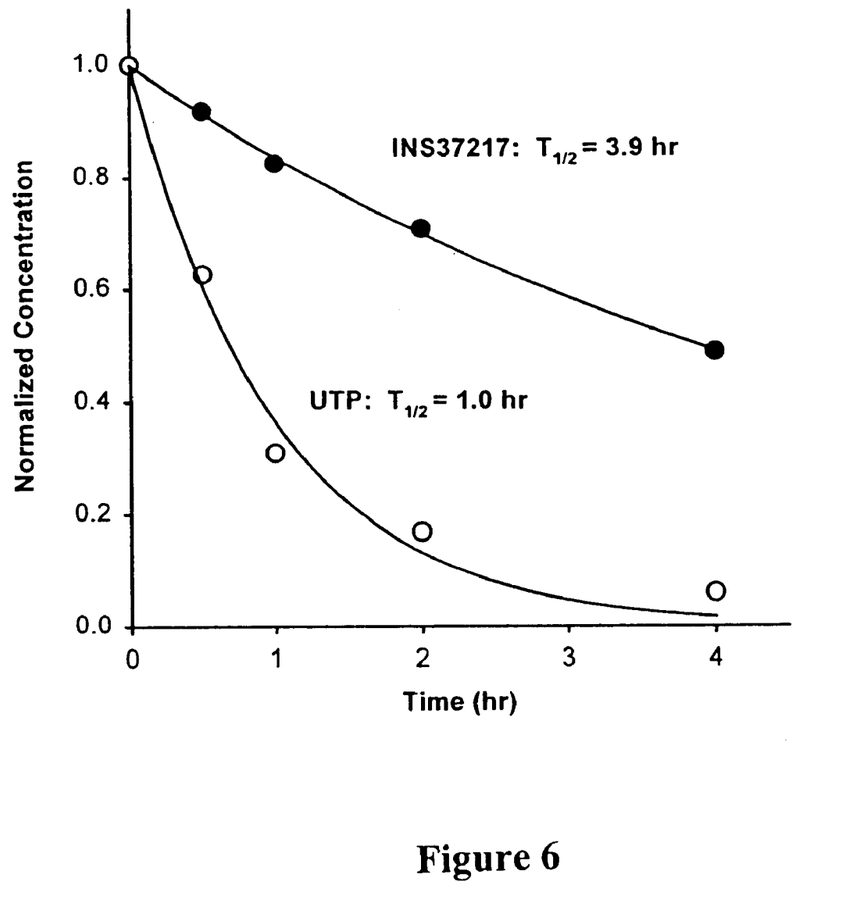
FIG. 6 represents the metabolism rates of INS37217 ($UP_4dC$) and UTP from freshly isolated pig retinal tissue.

Comparisons of Metabolic Stability of UP$_4$dC (INS37217) and UTP in Freshly Isolated Retinal Tissue The metabolism rate of UP$_4$dC (INS37217) and UTP in freshly isolated pig retinal tissue was determined using a high performance liquid chromatography (HPLC) method with UV-coupled detection. Freshly isolated retinal tissues of uniform size were isolated from euthanized young pigs (2–3 months) and retinal tissues were individually placed in an incubation chamber at 37° C. After an equilibration period of 30 minutes, each tissue was spiked with 100 $\mu$M UP$_4$dC or UTP in physiological buffer, and incubated at for 0.5, 1, 2, and 4 hours. An aliquot of buffer from each chamber well was then processed for UV-coupled HPLC detection for chromatograms of the parent UP$_4$dC and UTP compounds at each time point to track the metabolism rates of each parent compound. FIG. 6 shows that UP$_4$dC has a four-fold greater metabolic half-life than UTP under these experimental conditions.

EXAMPLE 5

UP$_4$dC (INS37217) Facilitates Retinal Reattachment in Rat and Rabbit Retinal Bleb Models Subretinal space blebs were experimentally created in Long-Evans pigmented rats and in New Zealand albino rabbits to mimic the effects of retinal detachment and to test the effects of UP$_4$dC (INS37217) in facilitating retinal reattachment in these bleb models. Production of subretinal blebs in Long-Evans rats using a specially developed, modified phosphate buffered saline (PBS) solution produced long-lasting blebs that would generally not resolve on their own over the course of many hours or overnight. To determine if UP$_4$dC enhanced subretinal bleb reabsorption, a series of masked, randomized, placebo-controlled experiments was conducted to compare the effects of UP$_4$dC to vehicle. Vials that contained either UP$_4$dC (5 mM) or vehicle were prepared under randomized conditions and each vial was marked such that the contents were coded and masked from the experimenter. The contents of the vials were indistinguishable. In this series of experiments, 3 µL of PBS was first injected into the subretinal space, and bleb volume was observed to remain constant for 30 minutes. Then 3 µL from a prepared vial was then injected into the vitreous, and bleb volume was observed after another 60 minutes and again at 24 hours. Bleb volumes were subjectively evaluated according to a scoring method of −3 to +3 at single unit intervals, with −3 representing complete reattachment of retina (no visible bleb) and +3 representing at least a doubling in the bleb size. Based on the 60 min and 24 hour evaluations, the experimenter made a decision as to the content of the vial (INS37217 or control) and recorded the decision in a lab notebook. All 12 experiments were completed before the treatment was unmasked. Under these conditions, the experimenter was able to correctly identify the content of all 12 vials based on the pharmacologically predictable response. The results from a total of twelve experiments are summarized in Table 1 below. Under these experimental conditions, UTP has no observable effect on retinal reattachment.

TABLE 1

Results of Masked Evaluation of UP$_4$dC (INS37217) vs. Vehicle Control on Bleb Reabsorption in a Rat Model of Retinal Detachment

| N* | 60 min | 24 h | Decision | Comments |
|---|---|---|---|---|
| 1 | +1 | 0 | control | |
| 2 | +2 | −1 | control | |
| 3 | −2 | −3 | UP$_4$dC | |
| 4 | −1 | −2 | UP$_4$dC | |
| 5 | +2 | 0 | control | |
| 6 | −2 | −3 | UP$_4$dC | |
| 7 | +1 | X | control | Cornea clouded @ 24 h |
| 8 | −1 | −2 | UP$_4$dC | |
| 9 | −1 | −3 | UP$_4$dC | |
| 10 | +1 | 0 | control | |
| 11 | −1 | −3 | UP$_4$dC | |
| 12 | +2 | 0 | control | |

*(N, animal designation number)

Similar retinal bleb experiments were conducted in New Zealand rabbits. Anesthetized rabbits were given a subretinal space injection of ~5 µL of modified phosphate buffered saline (PBS) solution with a 36-gauge retinal needle. After creating a single subretinal space bleb in each eye, one eye received an intravitreal injection of agonist and the contralateral eye received the control PBS solution. Subretinal space blebs were visualized via standard fundus examination with an indirect ophthalmoscope. Clearance of subretinal space blebs was evaluated by subjectively scoring the sizes of the blebs at 30-minute intervals relative to the size of the initial bleb. The nearby optic disk was used as a size marker to determine the relative width and length of each subretinal bleb. No information about the heights of blebs be ascertained using fundus examination.

Figure 7:
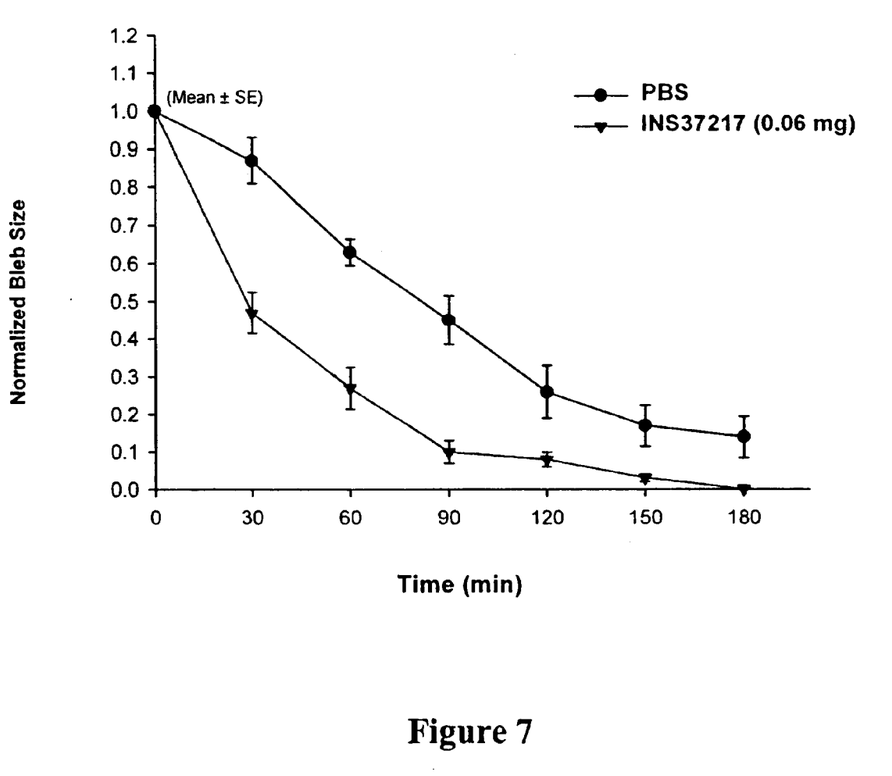
FIG. 7 represents the effects of INS37217 ($UP_4dC$) on subretinal fluid reabsorption in rabbits.

Rabbits used in these experiments have healthy retina and RPE. Control blebs exhibit a natural time course of clearance wherein the bleb is ~80% reduced in size over a period of 3 hours. (In patients with retinal detachment, the volume of the accumulation of subretinal space fluid generally remains constant over this time period) Despite the robust, natural clearance of subretinal blebs in rabbits, intravitreal administration of agonist a low concentration (FIG. 7) significantly increased the rates of bleb clearance and facilitated retinal reattachment when compared with intravitreal administration of PBS alone.

EXAMPLE 6

Primary Treatment for Subject with Macula-Off Rhegmatogenous Retinal Detachment A patient presents with sudden onset of loss of central vision and is diagnosed with macula-off rhegmatogenous retinal detachment with a single break in the superior retina that is less than one clock hour in size. The patient's conjunctiva (cul de sacs) is sterilized with topical Betadine and by scrubbing and draping the face and lashes and lids. Local anesthesia is given via subconjunctival injection of xylocaine. A patient is then given a single, slowly administered 50 µL-intravitreal injection of a sterile pharmaceutical composition by insertion of a 29 or 30 gauge needle from a 0.25 cc or 0.50 cc tuberculin syringe through the sclera in the pars plana region of the eye. The pharmaceutical composition consists of a metabolically resistant P2Y$_2$-receptor agonist formulated to isotonicity (280–300 mOsm) and physiological pH (7.0–7.5) in saline.

The patient's eyes are bilaterally patched and the patient remains rested in a horizontal position for 4 hours, at which the eyes are examined for retinal reattachment. If the retina has not completely reattached at the four hour time point, the patient's eyes remain bilaterally patched until the next day (20–24 hours post dosing), at which point the retina is reexamined for reattachment. Following retinal reattachment, the retinal tear is suitably treated by conventional methods such as cryotherapy or laser photocoagulation.

The invention, and the manner and process of making and using it, are now described in such fill, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of treating edematous retinal disorders, retinal detachment, or retinal edema, in a subject in need thereof, said method comprising:

administering to said subject a pharmaceutical composition comprising a P2Y receptor agonist or pharmaceutically acceptable salts thereof, in an amount effective to stimulate the removal of pathological fluid accumulation in intra-retinal and subretinal spaces associated with edematous retinal disorders, retinal detachment, or retinal edema, wherein said P2Y receptor agonist is a dinucleoside polyphosphate compound of Formula I:

Formula I wherein:

X is oxygen, methylene, difluoromethylene, or imido;

n=0, 1 or 2;

m=0, 1 or 2;

n+m=0, 1, 2, 3 or 4;

Z=OH or H;

Z'=OH or H;

Y=H or OH;

Y'=H or OH; and

B and B' are each independently a purine residue or a pyrimidine residue, as defined Formula Ia and Ib, respectively, linked through the 9- or 1-position, respectively:

Formula Ia wherein $R_1$ is selected from the group consisting of: hydrogen, chlorine, amino, monosubstituted amino, disubstituted amino, alkylthio, arylthio, or aralkylthio, where the substituent on sulfur contains up to a maximum of 20 carbon atoms, with or without unsaturation;

$R_2$ is selected from the group consisting of hydroxy, oxo, amino, mercapto, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, diacylamino, or $NHR_y$;

$R_x$ is O or is absent;

wherein $R_2$ is $NHR_y$, and $R_y$ and $R_x$ taken together form a 5-membered fused imidazole ring, optionally substituted on the 4- or 5-positions of the etheno moiety with alkyl, aryl or aralkyl moieties;

$R_3$ is hydrogen, azido, alkoxy, aryloxy, aralkyloxy, alkylthio, arylthio, or aralkylthio; or $A(C_{1-6}$ alkyl)$OCONH(C_{1-6}$ alkyl)B-wherein A and B are independently amino, mercapto, hydroxy or carboxyl; or pharmaceutically acceptable esters, amides or salts thereof;

J is carbon or nitrogen, with the provision that when J is nitrogen, $R_3$ is not present; and wherein alkyls are straight-chain, branched or cyclic;

wherein aryl groups are optionally substituted with lower alkyl, amino, alkylamino, $NO_2$, $N_3$, carboxylic, amido, sulfonamido, and halo groups; or Formula Ib wherein:

$R_4$ is selected from the group consisting of: hydrogen, oxo, hydroxy, mercapto, amino, cyano, $C_{7-12}$ arylalkoxy, $C_{1-6}$ alkylthio, $C_{1-6}$ alkoxy, $C_{1-6}$ alkylamino, and di$C_{1-4}$ alkylamino, wherein the alkyl groups are optionally linked to form a heterocycle;

$R_5$ is selected from the group consisting of: hydrogen, acetyl, benzoyl, $C_{1-6}$ alkyl, $C_{1-5}$ alkanoyl, and aroyl; optionally R, is not present;

$R_6$ is selected from the group consisting of: hydroxy, oxo, mercapto, $C_{1-4}$ alkoxy, $C_{7-12}$ arylalkoxy, $C_{1-6}$ alkylthio, S-phenyl, $C_{1-5}$ disubstituted amino, triazolyl, $C_{1-6}$ alkylamino, and di-$C_{1-4}$ alkylamino wherein said dialkyl groups are optionally linked to form a heterocycle or linked to $N_3$ to form a substituted ring; or $R_5$ and $R_6$ taken together form a 5-membered fused imidazole ring between positions 3 and 4 of the pyrimidine ring and form a 3, $N^4$-ethenocytosine derivative, wherein said etheno moiety is optionally substituted on the 4- or 5-positions with $C_{1-4}$ alkyl; phenyl; or phenyloxy; wherein at least one hydrogen of said $C_{1-4}$ alkyl; phenyl or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle;

$R_7$ is selected from the group consisting of: hydrogen, hydroxy, cyano, nitro, and $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with a substituent selected from the group consisting of: $C_{1-6}$ alkyl, phenyl, substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, and propenoic acid; or $R_6$ and $R_7$ together form a 5 or 6-membered saturated or unsaturated ring bonded through N or O or S at $R_6$, such ring optionally contains functional substituents; provided that when $R_8$ is amino or substituted amino, $R_7$ is hydrogen; and $R_8$ is selected from the group consisting of hydrogen, amino, di-$C_{1-4}$ alkylamino, $C_{1-4}$ alkoxy, $C_{7-12}$ arylalkoxy, $C_{1-4}$ alkylthio, $C_{7-12}$ arylalkylthio, carboxamidomethyl, carboxymethyl, methoxy, methylthio, phenoxy and phenylthio.

2. The method according to claim 1, wherein the furanosyl moiety of Formula I is a ribosyl or deoxyribosyl moiety.

3. The method according to claim 2, wherein said ribosyl or deoxyribosyl moiety is selected from the group consisting of: ribofuranosyl, arabinofuranosyl, 2'-deoxyribofuranosyl, 3'-deoxyfuranosyl, xylofuranosyl, and lyxofuranosyl.

4. The method according to claim 2, wherein the said furanosyl residue is in the beta-configuration.

5. The method according to claim 2, wherein the furanosyl residue is in the D-configuration.

6. The method according to claim 1, wherein said pharmaceutical composition is prepared in a formulation selected from the group consisting of: aqueous, gel, gel-like, and solid formulation.

7. The method according to claim 6, wherein said aqueous formulation further comprises physiologically safe excipients formulated to osmolarity between 250–350 mOsm and pH 5–9.

8. The method according to claim 6, wherein said aqueous formulation further comprises an intraocular irrigation solution approved for surgical use.

9. The method according to claim 6, wherein said gel or gel-like formulation is selected from the group consisting of: hyaluronic acid and hyaluronic acid-containing formulations approved for intraocular surgical use.

10. The method according to claim 6, wherein said solid formulation is selected from the group consisting of: lyophilized powder, liposome and biodegradable polymer.

11. A method of treating edematous retinal disorders, retinal detachment, or retinal edema, in a subject in need thereof, said method comprising:

administering to said subject a pharmaceutical composition comprising a P2Y receptor agonist or pharmaceutically acceptable salts thereof, in an amount effective to stimulate the removal of pathological fluid accumulation in intra-retinal and subretinal spaces associated with edematous retinal disorders, retinal detachment, or retinal edema, wherein said P2Y receptor agonist is selected from the group consisting of: $P^1$, $P^4$-di(uridine 5'-) tetraphosphate; $P^1$,$P^4$-di(adenosine 5'-)tetraphosphate; $P^1$-(adenosine 5')- $P^4$-(uridine 5'-) tetraphosphate; $P^1$-(adenosine 5')- $P^4$-(cytidine 5'-)tetraphosphate; $P^1$, $P^4$-di(ethenoadenosine) tetraphosphate; $P^1$-(uridine 5')-$P^4$-(thymidine 5'-)tetraphosphate; $P^1$-(adenosine 5') -$P^4$-(inosine 5'-)tetraphosphate; $P^1$, $P^4$-di(uridine 5')-$P^2$, $P^3$-methylenetetraphosphate; $P^1$, $P^4$-di(uridine 5')-$P^2$, $P^3$-difluoromethylenetetraphosphate; $P^1$, $P^4$-di (uridine 5')-$P^2$, $P^3$-imidotetraphosphate; $P^1$, $P^4$-di(4-thiouridine 5'-)tetraphosphate; $P^1$, $P^5$-di(uridine 5'-) pentaphosphate; $P^1$, $P^4$-di(3, $N^4$-ethenocytidine 5'-) tetraphosphate; $P^1$, $P^4$-di(imidazo[1,2-c]pyrimidine-5 (6H)-one-2-(3-nitro)-phenyl-6-β-D-ribofuranoside 5'-) tetraphosphate; $P^1$-(inosine 5')-$P^4$-(uridine 5'-) tetraphosphate; $P^1$-(cytosine β-D-arabinofuranoside 5') -$P^4$-(uridine 5'-)tetraphosphate; $P^1$-(uridine 5')-$P^4$- (xanthosine 5'-)tetraphosphate; $P^1$-(2'-deoxyuridine 5')-$P^4$-(uridine 5'-)tetraphosphate; $P^1$-(3'-azido-3'-deoxythymidine 5')-$P^4$-(uridine 5'-)tetraphosphate; $P^1$, $P^4$-di(3'-azido -3'-deoxythymidine 5'-)tetraphosphate; $P^1$, $P^6$-di(uridine 5'-)hexaphosphate; 2'(3')-benzoyl- $P^1$, $P^4$-di(uridine 5'-)tetraphosphate; $P^1$, $P^4$-di[2',(3')-benzoyl uridine 5'-]tetraphosphate; $P^1$-(2'-deoxyguanosine 5') -$P^4$-(uridine 5'-)tetraphosphate; $P^1$-(2'-deoxyadenosine 5')-$P^4$-(uridine 5'-)tetraphosphate; $P^1$-(2'-deoxyinosine 5') -$P^4$-(uridine 5'-)tetraphosphate; $P^1$-(4-thiouridine 5')-$P^4$-(uridine 5'-)tetraphosphate; $P^1$- (8-azaadenosine 5')-$P^4$-(uridine 5'-)tetraphosphate; $P^1$- (6-mercaptopurine riboside 5')-$P^4$-(uridine 5'-) tetraphosphate; $P^1$-(6-mercaptopurine riboside 5')-$P^4$- (2'-deoxyuridine 5'-)tetraphosphate; $P^1$-(4-thiouridine 5')-$P^4$-(cytosine-β-D-arabinofuranoside 5'-) tetraphosphate; $P^1$-(adenosine 5')-$P^4$-(4-thiomethyluridine 5'-)tetraphosphate; $P^1$-(2'-deoxyadenosine 5')-$P^4$- (6-thiohexylpurine riboside 5'-) tetraphosphate; $P^1$-(6-eicosanyloxypurine riboside 5')-$P^4$-(uridine 5'-)tetraphosphate; $P^1$-(uridine 5')-$P^3$-(4-thiouridine 5'-)triphosphate; and $P^1$-(uridine 5')-$P^2$-(4-thiouridine 5'-)diphosphate.

12. The method according to claim 1 or 11; wherein said P2Y receptor agonist is administered to achieve an intravitreal concentration range of about 1 micromolar to about 500 micromolar.

13. The method according to claim 1 or 11, wherein said pharmaceutical composition is co-administered with a primary treatment or adjunctive agents used to manage edematous retinal disorders.

14. The method according to claim 13, wherein said primary treatment is selected from the group consisting of: surgery, grid and focal laser photocoagulation, and pharmacotherapy.

15. The method according to claim 14, wherein said surgery is selected from the group consisting of: scleral buckling, pneumatic retinopexy, vitrectomy, and macular translocation.

16. The method according to claim 14, wherein said pharmacotherapy is selected from the group consisting of: corticosteroids, carbonic anhydrase inhibitors, anti-inflammatory agents, and pharmaceuticals that promote digestion of collagen and fibrous tissues that connect vitreous and retina.

17. The method according to claim 1 or 11, wherein said pharmaceutical composition is a sterile preparation further comprising a pharmaceutically acceptable carrier.

18. The method according to claim 17, wherein said pharmaceutically acceptable carrier is a physiologically compatible vehicle selected from the group consisting of: aqueous electrolyte solutions, polyethers, polyvinyls, polymers of acrylic acid, lanolin, and glucosaminoglycans.

19. The method according to claim 17, wherein said compound in said sterile preparation is in the form of particles ranging in size from 1 to 10 microns.

20. The method according to claim 1 or 11, wherein said pharmaceutically acceptable salts are selected from the group consisting of: sodium, chloride, potassium, calcium, magnesium, and bicarbonate.

21. The method according to claim 1 or 11, wherein said administering involves topical administration of said compound via a carrier vehicle selected from the group consisting of: drops of liquid, liquid wash, gels, ointments, sprays and liposomes.

22. The method according to claim 21, wherein said topical administration comprises infusion of said compound to said ocular surface via a device selected from the group consisting of: a pump-catheter system, a continuous or selective release device, and a contact lens.

23. The method according to claim 1 or 11, wherein said administering is systemic administration of said compound.

24. The method according to claim 23, wherein said systemic administration is administering a liquid or liquid suspension of said compound via nose drops or nasal spray or nebulized liquid to oral or nasopharyngeal airways of said subject, such that a therapeutically effective amount of said compound contacts the ocular tissues of said subject via systemic absorption and circulation.

25. The method according to claim 23, wherein said systemic administration is administering an oral form of said compound, such that a therapeutically effective amount of said compound contacts the ocular tissues of said subject via systemic absorption and circulation.

26. The method according to claim 23, wherein said systemic administration is administering an injectable form of said compound, such that a therapeutically effective amount of said compound contacts the ocular tissues of said subject via systemic absorption and circulation.

27. The method according to claim 26, wherein said compound is administered by injection into the vitreous, bolus or sustained infusion into the vitreous, by sustained release into the vitreal cavity, by retrobulbar conjunctival injection, release, or infusion, by transcleral injection, by sustained transcleral release or infusion, by ocular surface instillation, and by acute or chronic injection or infusions.

28. The method according to claim 27, wherein injection into the vitreous is by single or multiple intravitreal injections at injection volumes of 50–100 microliter.

29. The method according to claim 26, wherein injectable form is administered with an amount of between about 0.10 milligrams and about 4.0 milligrams of said compound per eye; wherein said pharmaceutically acceptable salts are sodium and chloride salts, and said pharmaceutical composition has an osmolarity between about 280 and 300 mOsm, and pH between about 7.0 and 7.6.

30. The method according to claim 23, wherein said systemic administration of said compound is administering a suppository form of said compound, such that a therapeutically effective amount of said compound contacts the ocular tissues of said subject via systemic absorption and circulation.

31. The method according to claim 23, wherein said systemic administration of said compound is administering an intra-operative instillation of a gel, cream, powder, foam, crystals, liposomes, spray or liquid suspension form of said compound, such that a therapeutically effective amount of said compound contacts the ocular tissues of said subject via systemic absorption and circulation.

32. The method according to claim 11, wherein said P2Y receptor agonist is selected from the group consisting of: $P^1$, $P^4$-di(uridine 5'-)tetraphosphate; $P^1$, $P^4$-di(adenosine 5'-)tetraphosphate; $P^1$-(adenosine 5')-$P^4$-(uridine 5'-)tetraphosphate; $P^1$-(adenosine 5')-$P^4$-(cytidine 5'-) tetraphosphate; $P^1$-(uridine 5')-$P^4$-(thymidine 5'-)tetraphosphate; $P^1$-(adenosine 5') -$P^4$-(inosine 5'-)tetraphosphate; $P^1$, $P^4$-di(uridine 5')-$P^2$, $P^3$-methylenetetraphosphate; $P^1$, $P^4$-di(uridine 5')-$P^2$, $P^3$-difluoromethylenetetraphosphate; $P^1$, $P^4$-di(uridine 5')-$P^2$, $P^3$-imidotetraphosphate; $P^1$, $P^4$-di(4-thiouridine 5'-)tetraphosphate; $P^1$-(inosine 5')-$P^4$-(uridine 5'-) tetraphosphate; $P^1$-(cytosine β-D-arabinofuranoside 5')-$P^4$-(uridine 5'-)tetraphosphate; $P^1$-(uridine 5')-$P^4$-(xanthosine 5'-)tetraphosphate; $P^1$-(2'-deoxyuridine 5') -$P^4$-(uridine 5'-)tetraphosphate; $P^1$-(3'-azido-3'-deoxythymidine 5')-$P^4$-(uridine 5'-)tetraphosphate; $P^1$-(2'-deoxyguanosine 5')-$P^4$-(uridine 5'-)tetraphosphate; $P^1$-(2'-deoxyadenosine 5')-$P^4$-(uridine 5'-)tetraphosphate; $P^1$-(2'-deoxyinosine 5')-$P^4$-(uridine 5'-)tetraphosphate; $P^1$-(4-thiouridine 5') -$P^4$-(uridine 5'-)tetraphosphate; $P^1$-(8-azaadenosine 5')-$P^4$-(uridine 5'-)tetraphosphate; $P^1$-(6-mercaptopurine riboside 5')-$P^4$-(uridine 5'-)tetraphosphate; $P^1$-(6-mercaptopurine riboside 5') -$P^4$-(2'-deoxyuridine 5'-)tetraphosphate; $P^1$-(adenosine 5')-$P^4$-(4-thiomethyluridine 5'-)tetraphosphate; $P^1$-(2'-deoxyadenosine 5')-$P^4$-(6-thiohexylpurine riboside 5'-)tetraphosphate; $P^1$-(uridine 5')-$P^3$-(4-thiouridine 5'-) triphosphate; and $P^1$-(uridine 5')-$P^2$-(4-thiouridine 5'-) diphosphate.

33. The method according to claim 32, wherein said P2Y receptor agonist is selected from the group consisting of: $P^1$, $P^4$-di(uridine 5'-)tetraphosphate; $P^1$-(adenosine 5')-$P^4$-(uridine 5'-) tetraphosphate; $P^1$-(adenosine 5')-$P^4$-(inosine 5'-)tetraphosphate; $P^1$, $P^4$-di(uridine 5')-$P^2$, $P^3$-difluoromethylenetetraphosphate; $P^1$, $P^4$- di(4-thiouridine 5'-)tetraphosphate; $P^1$-(inosine 5')-$P^4$-(uridine 5'-)tetraphosphate; $P^1$-(2'-deoxyuridine 5')-$P^4$-(uridine 5'-) tetraphosphate; $P^1$-(2'-deoxyguanosine 5')-$P^4$-(uridine 5'-) tetraphosphate; $P^1$-(2'-deoxyinosine 5')-$P^4$-(uridine 5'-) tetraphosphate; $P^1$-(4-thiouridine 5')-$P^4$-(uridine 5'-) tetraphosphate; and $P^1$-(adenosine 5')-$P^4$-(4-thiomethyluridine 5'-) tetraphosphate.

34. The method according to claim 33, wherein said P2Y receptor agonist is selected from the group consisting of: $P^1$, $P^4$-di (uridine 5'-)tetraphosphate; $P^1$-(adenosine 5') -$P^4$-(uridine 5'-)tetraphosphate; $P^1$-(inosine 5')-$P^4$-(uridine 5'-) tetraphosphate; $P^1$-(2'-deoxyguanosine 5')-$P^4$-(uridine 5'-) tetraphosphate; and $P^1$-(2'-deoxyinosine 5')-$P^4$-(uridine 5'-) tetraphosphate.

* * * * *